United States Patent [19]
Ash

[11] Patent Number: 5,906,978
[45] Date of Patent: May 25, 1999

[54] METHOD FOR IRON DELIVERY TO A PATIENT BY TRANSFER FROM DIALYSATE

[75] Inventor: Stephen R. Ash, Lafayette, Ind.

[73] Assignee: Hemocleanse, Inc., West Lafayette, Ind.

[21] Appl. No.: 08/869,331

[22] Filed: Jun. 5, 1997

Related U.S. Application Data

[60] Provisional application No. 60/023,926, Aug. 14, 1996.

[51] Int. Cl.$^6$ ......................... A61K 31/70; A61K 31/295; A61K 33/26
[52] U.S. Cl. ............................ 514/23; 424/648; 514/502; 514/814
[58] Field of Search ............................ 514/23, 502, 814; 424/648

[56] References Cited

U.S. PATENT DOCUMENTS

| | | |
|---|---|---|
| 3,686,397 | 8/1972 | Muller ...................................... 424/180 |
| 3,734,851 | 5/1973 | Matsumura . |
| 4,038,413 | 7/1977 | Suschitzky et al. ..................... 424/295 |
| 4,167,564 | 9/1979 | Jensen ...................................... 424/177 |
| 4,581,141 | 4/1986 | Ash ......................................... 210/502 |
| 4,659,697 | 4/1987 | Tanaka ..................................... 514/23 |
| 4,732,889 | 3/1988 | Cynshi et al. ............................... 514/8 |
| 4,810,695 | 3/1989 | Conti et al. ................................ 514/55 |
| 4,834,983 | 5/1989 | Hider et al. .............................. 424/463 |
| 4,970,079 | 11/1990 | Hem et al. ............................... 424/646 |
| 5,028,411 | 7/1991 | Callingham et al. ...................... 424/45 |
| 5,063,205 | 11/1991 | Peters et al. ............................... 514/12 |
| 5,177,068 | 1/1993 | Callingham et al. .................... 514/184 |
| 5,277,820 | 1/1994 | Ash ......................................... 210/646 |
| 5,336,506 | 8/1994 | Josephson et al. ...................... 424/488 |

OTHER PUBLICATIONS

Intraperitoneal Iron–Dextran As A Potential Route Of Iron Therapy In CAPD Patients—PDI Nov. 1996, vol. 16, No. 6, pp. 646–648.
Artificial Kidney—The Biomedical Engineering Handbook, Ch. 126, pp. 1898–1922.
Peritoneal Dialysis Equipment—The Biomedical Engineering Handbook, Ch. 127, pp. 1923–1935.

*Primary Examiner*—Leonard Schenkman
*Attorney, Agent, or Firm*—Woodard, Emhardt, Naughton Moriarty & McNett

[57] ABSTRACT

The invention relates to methods and compositions for delivering iron to an iron-deficient patient, more particularly, to methods whereby an iron complex comprising divalent or trivalent ionic iron complexed with one or more low molecular weight anions is administered to a patient by transfer from dialysate. A complex selected according to the invention is non-polymeric; soluble in an aqueous medium; chemically stable, thereby preventing the dissociation of iron ions from the anions under conditions according to the invention; and can be well absorbed into blood and the living body. Also provided are dialysate compositions including therein an iron complex selected according to the invention, and dialysate concentrates which may be diluted to yield an inventive dialysate composition.

20 Claims, 3 Drawing Sheets

METHOD FOR IRON DELIVERY TO A PATIENT BY TRANSFER FROM DIALYSATE

This application claims benefit of provisional application Ser. No. 60/028,926, filed Aug. 14, 1996.

BACKGROUND OF THE INVENTION

1. Field of the Invention

This invention relates to methods and compositions for efficiently delivering iron to a patient. More particularly, the present invention is concerned with dialysates and dialysate concentrates, and methods for delivering to a patient via dialysis a composition comprising ionic iron complexed with one or more anions. An iron complex selected according to the invention is non-polymeric; soluble in an aqueous medium; chemically stable, thereby preventing the dissociation of iron ions from the anions under conditions according to the invention; and can be well absorbed by blood and the living body.

2. Description of Related Art

Iron is a metal which is an essential requirement for tissue growth in humans and many animals. Therefore, an adequate supply of iron is critical to their survival and well-being. Although there is normally an ample amount of iron in the diet, the level of absorption of iron from food is generally low and, therefore, the supply of iron to the body can easily become critical under a variety of conditions. For example, iron is a necessary ingredient in the production of red blood cells, and a lack of iron may quickly lead to anemia. Iron deficiency anemia is commonly encountered, for example, in pregnancy and may also present a problem in the newly born. Moreover, in certain pathological conditions there is a maldistribution of body iron leading to a state of chronic anemia. This is seen in chronic diseases such as rheumatoid arthritis, certain haemolytic diseases and cancer.

Anemia is also uniformly present in patients with end stage renal disease (ESRD). The major cause of this anemia is the deficient production of erythropoeietin hormone (EPO) by the native kidneys. EPO stimulates the bone marrow to produce red cells, and when EPO is deficient, patients invariably become anemic. To counter the anemia of ESRD patients, recombinant EPO (which is very expensive) may be administered subcutaneously or intravenously. Recombinant EPO can effectively increase the hematocrit of patients with adequate iron stores, but the increased rate of production of new red cells quickly depletes body iron stores and, when this occurs, EPO becomes completely ineffective. As such, the delivery of iron to an ESRD patient is critical to his or her treatment. Methods in the prior art for delivering iron to a patient, such as an ESRD patient, have proven largely impractical and unsatisfactory, and there is a great need for improved methods of iron delivery.

It is well known that iron is very difficult to assimilate into the cells of a living organism and when an iron deficiency exists, oral iron supplements in relatively large doses are commonly administered wherein the iron may be in a wide variety of forms, i.e., usually as various organic and inorganic salts. Iron compositions which have been previously administered orally include, for example, ferrous gluconate, ferrous citrate, ferrous sulfate, ferrous fumarate and ferric-polysaccharide complexes. As a specific example of a condition where oral iron delivery is common, ESRD patients are typically directed to take oral iron tablets when EPO is started, as discussed above.

Oral iron administration, however, has several disadvantages. Patient noncompliance, gastrointestinal side effects, interactions with other oral medications and very poor absorption in ESRD patients markedly limit its effectiveness. For example, patients often stop taking these medications because of side effects associated therewith, such as constipation and gastric irritation. Additionally, these oral iron preparations cause a patient's stools to turn black, thereby making it difficult for caregivers to detect gastrointestinal bleeding during iron therapy. It is believed that these problems are all related to the administration of relatively high dosage levels of oral compounds due to the low level of iron uptake by the body, and these high doses are thought to also cause siderosis of the gut wall.

To overcome the above-described problems with oral delivery of iron, a great deal of effort has been directed to developing iron delivery methods wherein iron-containing compositions are delivered parenterally, either by intravenous or intramuscular injection. In this regard, it is currently widely believed that compositions used for non-oral iron administration must be in macromolecular form. This mindset is based upon the belief that the use of macromolecules eliminates the problem of osmolarity in the case of intramuscular injection, and, in the case of intravenous injection, the belief that macromolecular compositions are required to ensure that free iron is not introduced into the blood. Since iron is slowly freed from such macromolecules by the action of metabolism, and then bound by transferrin in the blood as it slowly becomes available, administration of iron in macromolecular forms is presently thought to be the only viable option with respect to intravenous administration techniques.

With respect to intravenous administration, iron-dextran (INFED®), which may be obtained from Schein Pharmaceuticals, Phoenix, Arizona, is commonly administered intravenously to ESRD patients to increase iron stores, with about 100–200 mg injected each successive dialysis until about 1000 mg are administered. Iron dextran is a macromolecule having a high average molecular weight ranging generally between about 100,000 and about 200,000. However, iron dextran occasionally causes severe allergic reactions, fever and rashes during injection and must therefore be administered slowly and after a small test dose. Ferric gluconate is another macromolecular iron complex for intravenous administration, and is relatively free of symptoms. However, each of these intravenous iron preparations is very expensive and requires a great deal of time and skill for administration. The large expense related to these intravenous preparations is associated in part with the necessity for sterilization of the injectant. Additionally, intravenous administration requires venous access, which is available during hemodialysis, but not commonly available in peritoneal dialysis patients. Finally, only about half of iron in iron dextran is bio-available after intravenous injection for red cell production. The fate of the rest is unknown.

With respect to intramuscular injection, iron dextrins and iron dextrans may be administered intramuscularly; however, as a result of their high molecular weights, absorption in the human or animal body is incomplete. Furthermore, the administration of these compositions intramuscularly is painful and often results in an undesirable discoloration at the injection site. Alternatively, U.S. Pat. No. 3,686,397 to Muller teaches an iron preparation for intramuscular injection which comprises a nonionic complex of trivalent iron supplied a ferric hydroxide with a complex forming agent consisting of sorbitol, gluconic acid and certain oligosaccharides (polyglucoses) in certain proportions and amounts. Other macromolecular iron preparations which may be administered via intramuscular injection are taught in U.S. Pat. No. 5,177,068 to Callingham et al., U.S. Pat. No. 5,063,205 to Peters et al., U.S. Pat. No. 4,834,983 to Hider et al. and U.S. Pat. No. 4,167,564 to Jenson. Many preparations, such as that taught in the Jenson patent, may be administered parenterally either by intramuscular or intravenous injection.

Recently, it has been proposed that iron may be administered to a mammal by intraperitoneal delivery of macromolecular iron dextran. It has been found that only about half of the iron delivered intraperitoneally in this form is bioavailable, passing to the blood and then to the reticuloendothelial system and bone marrow, where it is incorporated into red cells. It appears that about 50% of the iron dextran is stored permanently in the body and is not available for red cell production. There is evidence that macrophages near the peritoneum pick up iron-dextran and store it within themselves, creating an abnormal physical condition which could lead to abnormal membrane changes in the peritoneum.

In light of this background, there is a great need in the art for improved methods for delivering iron to a patient. The present invention addresses the problems in the prior art by providing methods and compositions for delivering iron by transfer of a low molecular weight (non-polymeric) iron complex from dialysate. Inventive methods are surprisingly effective in light of conventional thought, which teaches that complexes selected according to the invention do not have sufficient solubility to be useful in this manner. Further, it is widely believed that soluble iron complexes are unacceptable iron delivery agents, this belief being based upon a fear of the toxicity of free iron in blood.

The present inventor has discovered that iron complex compositions selected in accordance with the invention are tightly complexed and are highly soluble, and can thereby be safely administered to a patient using dialysis with minimal staff effort and very little risk. This high solubility also advantageously allows an inventive complex to be included in dialysate concentrates, which are described in greater detail herein. For hemodialysis applications, the iron can be added to a dialysate or a concentrate, just as other solutes, in "clean" form and need not be sterilized. For peritoneal applications, the iron composition can be sterilized.

SUMMARY OF THE INVENTION

The present invention provides methods and compositions for delivering iron to an iron-deficient patient. More particularly, the invention relates to delivering to a patient via dialysis a composition comprising ionic iron complexed with one or more anions, wherein the complex is non-polymeric; soluble in an aqueous medium; chemically stable, thereby preventing the dissociation of iron ions from the anions under conditions according to the invention; and can be well absorbed by blood and the living body.

According to one specific aspect of the invention, there is provided a method for performing dialysis with a complex of one or more divalent or trivalent iron ions and one or more anions, the complex having a molecular weight of less than about 50,000 and preferably being non-polymeric. This method of delivering iron to a patient comprises providing an aqueous dialysate having the complex dissolved therein, and dialyzing a patient with the dialysate to increase the level of iron in the patient's blood. Inventive methods achieve this advantageous result without introducing free iron into the blood. A preferred anion according to one aspect of the invention is an organic anion.

According to another aspect of the invention, there is provided a method for delivering iron to blood which comprises passing blood against a first side of a membrane and passing against a second side of the membrane an aqueous solution having dissolved therein an iron complex comprising one or more iron ions and one or more anions, the complex having a molecular weight of less than about 12,000; wherein the membrane is permeable to the complex and wherein the complex is delivered to the blood.

According to another aspect of the invention, there is provided a method for increasing the level of iron in a patient's blood by introducing a dialysate into a patient's peritoneal cavity, the dialysate comprising a non-polymeric complex of one or more divalent or trivalent iron ions and one or more anions, the complex having a molecular weight of less than about 50,000.

In another aspect of the invention, there is provided a dialysate composition having dissolved therein sodium, magnesium, calcium, potassium, chloride, acetate, bicarbonate and an iron complex having a molecular weight of less than about 50,000. An inventive dialysate comprises from about 130 to about 150 mEq/L sodium, from about 0.4 to about 1.5 mEq/L magnesium, from about 2 to about 4 mEq/L calcium, from about 1 to about 4 mEq/L potassium, from about 90 to about 120 mEq/L chloride, from about 3 to about 5 mEq/L acetate, from about 30 to about 40 mEq/L bicarbonate and from about 1 to about 250 $\mu$g/100 ml of iron as an iron complex having a molecular weight of less than about 50,000. Also provided is a dialysate concentrate, prepared for subsequent dilution to a suitable concentration for use as a dialysate, preferably having a concentration about 30 to about 40 times greater than the concentration of the desired dialysate.

It is an object of the present invention to provide improved methods for administering iron to a patient, especially a patient suffering from chronic anemia and end stage renal disease.

Another object of the invention is to provide methods whereby conventional hemodialysis techniques may be used to deliver iron to a patient without the need to sterilize the iron-containing composition prior to administration.

It is also an object of the invention to provide methods for delivering iron to peritoneal dialysis patients by providing a dialysate which includes sterile non-polymeric iron complexes according to the invention.

Additionally, it is an object of the invention to provide dialysate compositions which may be advantageously used to deliver iron to a patient by a wide variety of dialysis techniques and concentrates thereof.

Further objects, features, and advantages of the present invention shall become apparent from the detailed drawings and descriptions provided herein.

BRIEF DESCRIPTION OF THE DRAWINGS

Although the characteristic features of this invention will be particularly pointed out in the claims, the invention may be better understood by referring to the following descriptions taken in connection with the accompanying drawings forming a part hereof.

DESCRIPTION OF THE PREFERRED EMBODIMENT

For the purposes of promoting an understanding of the principles of the invention, reference will now be made to the preferred embodiments and specific language will be used to describe the same. It will nevertheless be understood that no limitation of the scope of the invention is thereby intended. Any alterations and further modifications in the described invention, and any further applications of the principles of the invention as described herein are contemplated as would normally occur to one skilled in the art to which the invention relates.

The present invention overcomes problems in the prior art associated with delivering iron to a patient. Iron delivery according to the invention is accomplished by providing a dialysate composition comprising a iron complex which is soluble in an aqueous medium and delivering the complex to a patient using conventional dialysis techniques. An "iron complex," as used herein, is intended to designate a composition comprising one or more iron ions complexed with one or more suitable anions and having a molecular weight of less than about 50,000. Inventive iron complexes are preferably non-polymeric.

This invention, therefore, relates to surprisingly efficacious methods for delivering iron by providing a dialysate, the dialysate advantageously being prepared either by on-site preparation or by diluting a pre-made dialysate concentrate and the dialysate having dissolved therein, among other solutes, a low molecular weight non-polymeric iron complex; and dialyzing a patient therewith using one of a wide variety of dialysis techniques. Inventive methods are useful for delivering iron to a patient in readily-available form and, since iron complexes according to the invention are relatively tightly bound, they may advantageously be delivered to a patient without risk of introducing free iron into the blood. It is contemplated that various compositions, compositional ratios, procedures, and processes described in connection with the present invention could be altered or substituted as would occur to those skilled in the art without departing from the spirit of the invention. It is believed that inventive methods may advantageously be used in conjunction with dialysis techniques currently in wide use, as well as improvements thereof, and with dialysis techniques yet to be developed. It is anticipated that the present invention may find particularly advantageous use in hemodialysis procedures and intraperitoneal dialysis procedures.

With regard to specific examples of dialysis techniques, it is well known that conventional hemodialysis procedures may be performed in free-standing treatment centers, although they may also be provided in a hospital or performed by the patient at home. Conventional hemodialysis circuits have two fluid pathways: the blood circuitry and the dialysate circuitry. The blood circuitry conventionally comprises a 15-gauge needle for access to the circulation (usually through an arteriovenous fistula created in the patient's forearm), lengths of plasticized polyvinyl chloride tubing (including a special segment adapted to fit into a peristaltic blood pump), the hemodialyzer itself, a bubble trap and an open mesh screen filter, various ports for sampling or pressure measurements at the blood outlet, and a return cannula. Access to the circulation may alternatively be made at a single access point using a double-lumen catheter. Components of the blood side circuit are supplied in sterile and nonpyrogenic condition. The dialysate side typically comprises a machine capable of (1) proportioning out glucose and electrolyte concentrates with water to provide a dialysate of appropriate composition; (2) pulling dialysate past a restrictor valve and through the hemodialyzer at subatmospheric pressure; and (3) monitoring temperature, pressures, and flow rates.

During treatment the patient's blood is typically anticoagulated with heparin. Typical blood flow rates are about 200–350 ml/min and dialysate flow rates are usually set at about 500 ml/min. A dialysate volume of about 120–200 liters is typically used per dialysis treatment. Simple techniques have been developed to prime the blood side with sterile saline prior to use and to return to the patient nearly all the blood contained in the extracorporeal circuit after treatment. Whereas most mass transport occurs by diffusion, circuits are typically operated with a pressure on the blood side, which may be 100–500 mmHg higher than on the dialysate side. This provides an opportunity to remove 2–4 liters of fluid along with solutes in a single treatment. Higher rates of fluid removal are technically possible but physiologically unacceptable. Hemodialyzers must be designed with high enough hydraulic permeabilities to provide adequate fluid removal at low transmembrane pressure but not so high that excessive water removal will occur in the upper pressure range.

Although other geometries may be employed, one preferred hemodialyzer format is a "hollow fiber" hemodialyzer about 25 cm in length and 5 cm in diameter, resembling the design of a shell and tube heat exchanger. Blood enters this type of hemodialyzer at an inlet manifold, is distributed to a parallel bundle of capillary tubes (typically potted together with polyurethane), and exits at a collection manifold. Dialysate flows countercurrent in an external chamber. The shell is typically made of an acrylate or polycarbonate resin. Devices typically contain about 6000–10,000 capillaries, each with an inner diameter of about 200–250 microns and a dry wall thickness as low as about 10 microns. The total membrane surface area in commercial dialyzers typically varies from about 0.5 to about 1.5 $m^2$, and units can be mass-produced at a relatively low cost.

Although a specific hemodialysis set-up is described in detail above, it is well understood that a wide variety of hemodialysis devices may be advantageously used in accordance with the invention. Examples of alternate hemodialysis devices and methods suitable for use according to the invention are set forth in U.S. Pat. No. 5,277,820 to Ash; U.S. Pat. No. 4,661,246 to Ash; U.S. Pat. No. 4,581,141 to Ash; U.S. Pat. No. 4,348,283 to Ash; U.S. Pat. No. 4,071, 444 to Ash et al.; U.S. Pat. No. 3,734,851 to Matsumura; U.S. Pat. No. 4,897,189 to Greenwood et al.; U.S. Pat. No. 4,267,041 to Schael; U.S. Pat. No. 4,118,314 to Yoshida; U.S. Pat. No. 3,989,625 to Mason; and U.S. Pat. No. 3,962,075 to Fialkoff et al. These patents are hereby incorporated herein by reference.

In a hemodialysis treatment, as discussed above, blood is removed from the body, propelled through a closed system of membranes, and returned to the body, while on the other side of the membranes is an aqueous dialysis fluid. These membranes are semipermeable, allowing small molecules to pass through, but retaining larger molecules such as proteins, as well as cellular blood elements. Uremic substances, being small molecules, will pass through the membranes as long as the concentration of these substances is kept low in the dialysis fluid, or dialysate, on the other side of the membrane. The aqueous medium so used must be prior treated to remove trace elements (which would otherwise pass back across the membrane into the blood), must be supplemented with electrolytes and glucose, and must then be warmed to blood temperature. The electrolytes are added to the dialysate so as to prevent excessive ion removal (i.e., $Mg^{++}$, $K^+$, $Na^+$, $Cl^-$ and $HC_3^{31}$). Calcium ions should also be in slight excess in the dialysate so as to cause addition of calcium to the patient's blood, as the total body calcium in kidney failure patients is often low, leading to stimulation of parathyroid hormone, which is detrimental to the patient's health.

In one preferred aspect of the present invention, a non-polymeric iron complex is used according to the invention in conventional extracorporeal hemodialysis techniques by providing a dialysate, for example, as described above, having the iron complex dissolved therein to a predetermined concentration. An iron complex to be dissolved into dialysate for hemodialysis must be "clean," but need not be sterile, as is the case for other solutes in a dialysate. This provides a substantial advantage over prior methods of iron delivery to a patient by intramuscular or intravenous injection, both of which necessitate that the iron preparation be sterilized prior to injection. The dialysate, having a clean iron complex dissolved therein will deliver the iron complex to the blood during dialysis by diffusion, at a rate automatically responding to the blood plasma concentration, just as the concentrations of other solutes (such as, for example, sodium, potassium, glucose, bicarbonate, magnesium, calcium and chloride) are adjusted in dialysate to assure proper plasma levels in a patient. In the case of inventive iron complexes, however, it appears that blood proteins are binding the complex, thereby removing the complex from the plasma water and maintaining a concentration gradient between the dialysate and the blood. Basis for this theory is found in Example 1 and FIG. 1, where it is shown that the total amount of ferrous gluconate transferred to blood is higher than that expected based upon simple concentration gradient analysis. Thus, transfer of an inventive iron complex to the blood will continue until the level of free iron complex in the plasma reaches the same concentration as the iron complex dissolved in dialysate.

Turning now to an alternate dialysis technique, another type of dialysis with which inventive methods may be advantageously used is continuous ambulatory peritoneal dialysis (CAPD), also referred to herein interchangeably as "peritoneal dialysis" or "intraperitoneal dialysis." In this type of dialysis, approximately 2 liters of a sterile, nonpyrogenic, and hypertonic solution of glucose and electrolytes are instilled via gravity flow into the peritoneal cavity of a patient through an indwelling catheter, typically 4 times per day. Intraperitoneal fluid partially equilibrates with solutes in the plasma, and plasma water is ultrafiltered due to osmotic gradients. After about 4–5 hours, except at night where the exchange is lengthened to about 9–11 hours to accommodate sleep, the peritoneal fluid is drained and the process repeated. Patients may perform the exchanges themselves in about 20–30 minutes, for example at home or in the work environment, after a training cycle which usually lasts about 1–2 weeks. Alternatively, automated peritoneal dialysis (APD) may be used, in which case about 10–15 liters of dialysate are automatically exchanged overnight and 2 liters remain in the peritoneal cavity during the day for a "long dwell" exchange.

Access to the peritoneum is usually via a double-cuff Tenckhoff catheter, essentially a 50–100 cm length of silicone tubing with side holes at the internal end, a dacron mesh flange at the skin line, and connector fittings at the end of the exposed end. A wide variety of variations exist, however, and may advantageously be used in accordance with the invention. Most are implanted in a routine surgical procedure requiring about 1 hour and are allowed to heal for about 1–2 weeks prior to routine clinical use. Sterile and nonpyrogenic fluid is commonly supplied in 2 liter containers fabricated from dioctyl phthalate plasticized polyvinyl chloride. The formulation is essentially potassium-free lactated Ringers to which has been added from about 15–42.5 grams/liter of glucose (dextrose monohydrate). The solution is buffered to a pH of about 5.1–5.5, since the glucose would caramelize during autoclaving at higher pH levels.

Several different exchange protocols may be used in a peritoneal dialysis procedure. In one conventional design, the patient simply rolls up the empty bag after instillation and then drains into the same bag following exchange. The bag filled with drain fluid is disconnected and a fresh bag is reconnected. Patients are trained to use aseptic technique to perform the connect and disconnect. Many aids have been developed to assist in minimizing breaches of sterility including enclosed ultraviolet-sterilized chambers and heat splicers. More recent approaches, known as the "O" set and "Y" set or more generically as "flush before fill" disconnect, invoke more complex tubing sets to allow the administration set to be flushed (often with antiseptic) prior to instillation of dialysate and generally permit the patient to disconnect the empty bag during the dwell phase. Initial reports of the success of these protocols in reducing peritonitis were regarded with skepticism, but improvement over earlier systems has now been documented in well-designed and carefully controlled clinical trials.

Iron complexes selected in accordance with the invention may also be administered to a patient from dialysate intraperitoneally, for example, as described above. While dialysates used for intraperitoneal dialysis must be sterilized prior to use, this aspect of the invention also provides an excellent manner in which to introduce iron complexes into a patient's blood in an advantageous form. In intraperitoneal dialysis techniques, just as in hemodialysis techniques, a smaller iron complex will move more readily from the dialysate into the patient's blood than will a larger complex.

While the term "dialysate" is used interchangeably in various contexts, for instance, with respect to hemodialysis and with respect to peritoneal dialysis, it is readily understood by a skilled artisan that a variety of solutes and concentrations of solutes may be used with respect to various dialysis techniques, and also may vary with respect to the particular needs of a given patient. Because an iron complex selected for use according to the invention is absent in native blood, its presence in dialysate results in diffusion from the dialysate into the blood. This diffusion is augmented in preferred aspects of the invention by the apparent binding of the iron complex to plasma proteins.

It should be pointed out that the term "complex" may have alternate meanings in various contexts in the related art and, therefore, clarification of its meaning for purposes of describing the invention is in order. At one level, the term "complex" may be used to describe the association between two or more ions to form a relatively low molecular weight non-polymeric composition which exists singly under a given set of conditions. This type of complex may be referred to as a "primary complex," and this is the manner in which the term is to be used herein. As such, the term "primary complex" is used interchangeably herein with the term "complex" for purposes of describing the invention. An alternate manner in which this term is used in the related field is to describe the association or agglomeration of a plurality of primary complexes into a large macromolecule, or "secondary complex." For purposes of simplicity, these agglomerates are referred to herein as macromolecules, and are not considered "complexes" as the term is used to describe the invention.

As an example of the above distinction, ferrous gluconate is a composition comprising divalent iron ions and gluconate anions. A divalent iron ion and two gluconate anions form a primary complex of relatively low molecular weight (about 450 Daltons) and primary complexes of this type do not become agglomerated into macromolecules when dissolved into an aqueous medium. Ferrous gluconate, therefore, is a composition which falls within the scope of the term "complex" herein. Ferric gluconate, however, does not exist as such a complex because primary complexes of trivalent iron ions and gluconate anions agglomerate together to form very large macromolecules (commonly having a molecular weight of between about 100,000 and 600,000 Daltons). As such, iron complexes according to the invention are identified by selecting a combination of one or more iron ions (either divalent or trivalent) and one or more anions which interact to form primary complexes, but do not become agglomerated into macromolecules.

As such, the present invention provides dialysate compositions, and methods of using them, which comprise a primary iron complex of one or more divalent or trivalent iron ions and one or more anions described herein; which does not become associated or agglomerated to form a macromolecule; which is soluble in an aqueous medium; and which has a molecular size and, correspondingly, a molecular weight, which imparts advantageous properties with respect to diffusion of the complex through a dialysis membrane.

With respect to solubility, the solubility of a given iron complex according to the present invention must be such that the concentration of the complex in a dialysate solution may be achieved which enables the desired level of iron delivery to the patient. While conventional belief in the relevant field is that complexes of the invention would not be sufficiently soluble in an aqueous medium to find advantageous use, the present inventor has discovered that preferred inventive complexes are highly soluble.

The particular concentration of iron complex to be dissolved in a dialysate according to the present invention is dependent upon the amount of iron desired to be transferred to the patient's blood. For example, the amount of iron desired to be transferred in the case of an anemic patient is associated with the known blood building requirements of the patient. In other words, to determine the desired concentration of the iron complex in the dialysate, it is first calculated how much iron the patient needs for building blood cells. The complex will transfer to the patient at a controlled, definable rate, since the iron complex does not exist naturally in the blood. As is readily understood by one skilled in the art, a higher concentration of iron complex would be needed in peritoneal dialysis techniques than that which would be needed in extracorporeal hemodialysis techniques due to differing rates of diffusion with respect to the respective membranes and due to the lower daily volume of dialysate used in peritoneal dialysis. Preferred concentrations in a given situation may be readily determined by a skilled artisan with minimal experimentation.

In a preferred aspect of the invention, iron complexes selected for use are sufficiently soluble in aqueous media to be advantageously included in a wide variety of formulations to make dialysate concentrates. As used herein, the term "concentrate" is intended to designate a solution wherein the solutes are dissolved therein at concentrations much greater (commonly about 30–40 times greater) than a desired dialysate concentrate. A dialysate concentrate, therefore, has a volume 30–40 times less than the actual dialysate and may therefore be pre-mixed and advantageously shipped and handled much more readily. At the location of a dialysis procedure, a concentrate is diluted to the proper volume, commonly in the dialysis instrument itself, thereby providing a dialysate having suitable solute concentrations for the particular use.

The high concentration of solutes in a dialysate concentrate results in a reduced amount of water which is available to dissolve additional solutes. Therefore, the most preferred iron complexes used in accordance with the invention are highly soluble. The use in the art of dialysate concentrates is apparently an additional factor which has engendered the belief that iron complexes, such as those selected in accordance with the invention, do not have sufficient solubility to be used as described herein. In contravention of this belief, the present inventor has discovered, for example, that ferrous gluconate is stably soluble in such a concentrate at levels over 8 grams per 100 ml (dl), thus providing an iron concentration of about 1 gram per 100 ml. As is readily ascertainable by one skilled in the art, this would result in an iron concentration in dialysate of approximately 30 mg (30,000 $\mu$g) per 100 ml after a 35:1 dilution.

An iron complex contemplated for use according to the present invention comprises one or more divalent or trivalent iron ions relatively tightly bound to one or more anions to form a low molecular weight iron complex. As used herein, "relatively tightly bound" is intended to mean that the iron ion or ions and the anion or anions will not readily become dissociated under conditions of the present invention to yield free iron ions. The anion may be a natural or a synthetic molecule and may be either organic or inorganic, so long as it forms a primary complex with divalent or trivalent iron ions according to the present invention, but does not ultimately become associated into a macromolecule and so long as the anion is biocompatible. It is important that the iron ion and the anion remain tightly bound under relevant conditions because an overabundance of free iron ions in a dialysate and, as a result, in a patient's blood, may cause hemolysis and, if extreme, may cause death.

The anion of an iron complex selected in accordance with the invention is preferably a multi-polar anion, including for example a divalent or trivalent anion (e.g. di- or tricarboxylic acids (preferably aliphatic) having up to about 10 carbon atoms, optionally also substituted with one or more polar groups such as hydroxyl groups); or a monovalent anion which has additional polar substituents (such as hydroxyl groups) and which is readily complexed with iron ions, such as monohydroxycarboxylic or polyhydroxycarboxylic acids, typically having up to about 10 carbon atoms, especially aliphatic acids of this type such as gluconic acid. It is contemplated that suitable anions for iron complexes of the invention include, for example, gluconate, sulfate, fumarate, citrate and succinate. It is not intended, however, that this list be limiting, and it is within the purview of a skilled artisan to identify anions which form suitable iron complexes for advantageous use according to the invention.

The term "low molecular weight iron complex" is intended to designate an iron complex having a size useful for passing through dialysis membranes. As such, iron complexes selected according to the invention preferably have a molecular weight of less than about 50,000 and are preferably non-polymeric. This designation is intended to distinguish iron complexes selected according to the invention from large polymeric compositions and compositions in which primary complexes have become associated with one another to form macromolecules, as discussed above. This molecular weight limitation ensures that iron complexes used according to the present invention are of a size which will pass a wide variety of dialysis membranes used in a wide variety of dialysis methods. It is readily understood by a skilled artisan that many iron complexes selected according to the invention may be advantageously used in both hemodialysis techniques and in intraperitoneal dialysis techniques. Some iron complexes, however, such as those having a molecular weight greater than about 12,000, may not diffuse through many membranes used in hemodialysis to a suitable degree, but may nevertheless be advantageously used in intraperitoneal dialysis techniques.

With regard to intraperitoneal dialysis, it is expected that an iron complex having a molecular weight greater than about 50,000 will not be readily transported to the patient's blood. In a preferred aspect of the invention, therefore, the iron complex to be used for intraperitoneal dialysis has a molecular weight of less than about 50,000, preferably less than about 25,000, more preferably less than about 12,000 and most preferably less than about 5000.

With regard to extracorporeal hemodialysis methods, it is preferred that the iron complex have a molecular weight of less than about 12,000. More preferably, the iron complex has a molecular weight of less than about 5,000 and most preferably less than about 2,500. It is to be understood that the lower the molecular weight of the iron complex and, correspondingly, the smaller the iron complex, the faster the iron complex may be incorporated into a patient's blood.

Complexes selected for use according to the invention may be identified, therefore, by their molecular weight, by their degree of solubility in an aqueous medium and by their ability to remain tightly complexed under conditions of the invention. In this regard, a useful way to determine whether an iron-containing composition falls within the scope of the invention, is to introduce it into water and, using techniques well known to those skilled in the art, to test levels of solubility and to determine whether the complex becomes dissociated in solution.

According to another aspect of the invention, there is provided a dialysate composition having dissolved therein sodium, magnesium, calcium, potassium, chloride, acetate, bicarbonate and an iron complex having a molecular weight of less than about 50,000. In certain preferred embodiments of the invention, the dialysate may also optionally include dextrose, a sorbent and/or a surfactant. Preferably, the dialysate composition comprises from about 130 to about 150 mEq/L sodium, from about 0.4 to about 1.5 mEq/L magnesium, from about 2 to about 4 mEq/L calcium, from about 1 to about 4 mEq/L potassium, from about 90 to about 120 mEq/L chloride, from about 3 to about 5 mEq/L acetate, from about 30 to about 40 mEq/L bicarbonate and from about 1 to about 250 $\mu$g/dl iron as an iron complex having a molecular weight of less than about 50,000.

As discussed above, in the field of dialysate preparation, it is common for dialysates to be prepared at the site of dialysis, immediately before or simultaneously with the dialysis procedure, by diluting a pre-made "dialysate concentrate" having dissolved therein the desired solutes at a very high concentration. In this regard, dialysate concentrates, which are also considered to be a part of the present invention, are typically prepared such that the solutes have concentrations about 30–40 times greater than the desired concentration in the actual dialysate fluid, e.g. the preferred concentrations given above. The present inventor has discovered that certain iron complexes of the invention, such as, for example, ferrous gluconate, have excellent solubility and may find advantageous use in the preparation of dialysate concentrates.

In this respect, in another aspect of the invention, there is provided a dialysate concentrate comprising sodium, magnesium, calcium, potassium, chloride, acetate, bicarbonate and an iron complex having a molecular weight of less than about 50,000. In certain preferred embodiments of the invention, the concentrate may also optionally include dextrose, a sorbent and/or a surfactant. As stated above, the concentrate may then be diluted to the desired dialysate concentration, preferably in the dialysis apparatus itself, and the ratio of concentrate to diluent combined in the dilution apparatus may be carefully controlled to achieve the desired concentrations of materials dissolved in the dialysate. More preferably, the concentrate comprises the above compositions at concentrations from about 35 to about 45 times more concentrated than the desired dialysate concentration, even more preferably between about 34 and about 38 times more concentrated and, most preferably from about 35 to about 37 times more concentrated.

In a preferred aspect of the invention, the iron complex which is dissolved into a dialysate or a dialysate concentrate is ferrous gluconate. Ferrous gluconate is commercially available from Fluka Chemical Corporation, Chemika-Biochemika, 980 South Second Street, Ronkonkoma, New York, N.Y. 11779-7238. Ferrous gluconate has been found by the present inventor to be extremely soluble and to readily diffuse into blood through a dialysis membrane during conventional hemodialysis techniques. In this iron complex, two gluconate anions are tightly complexed with a ferrous ion in the presence of water.

Figure 1:
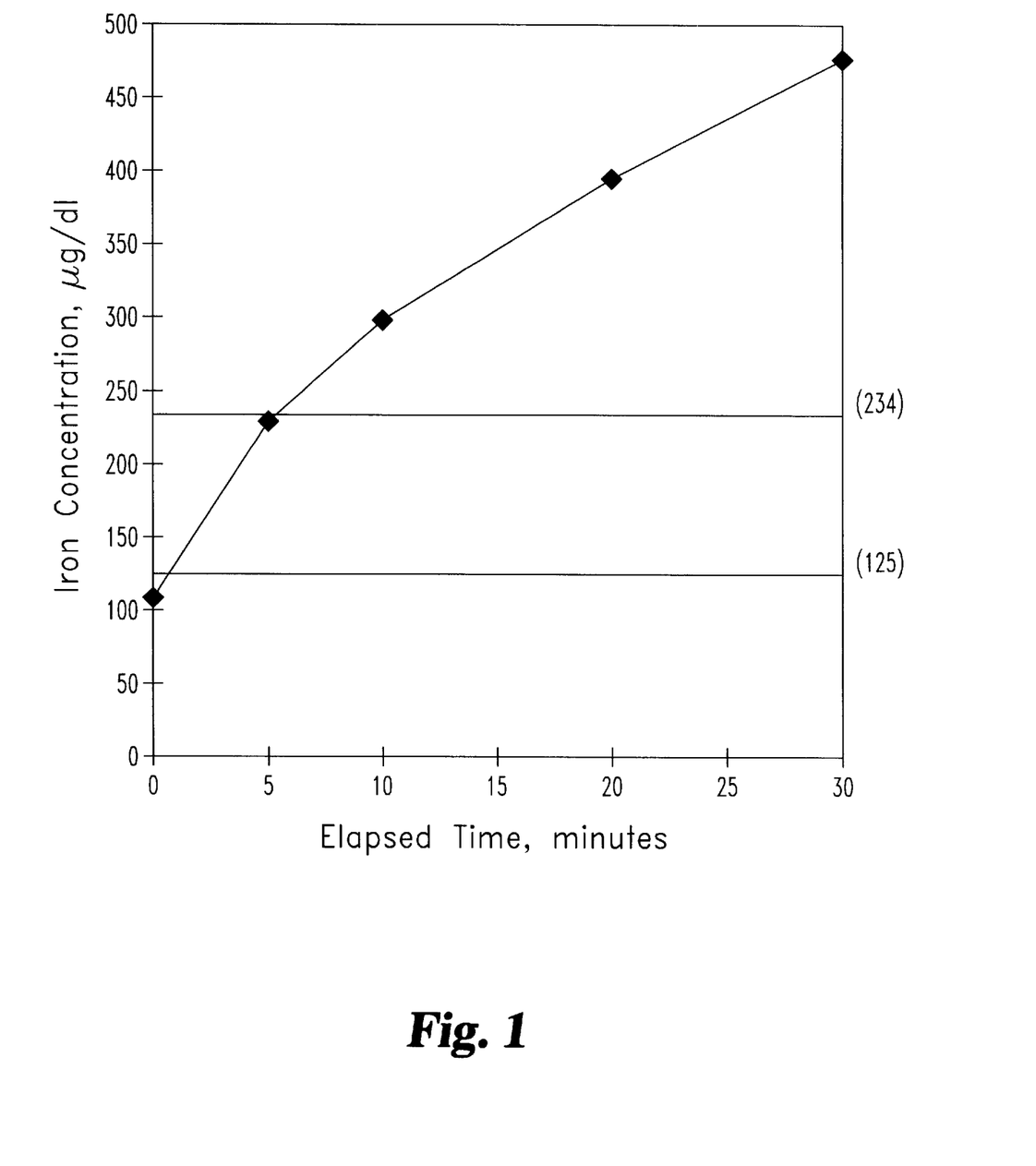
FIG. 1 is a plot of iron concentration ($\mu$g/dl) in plasma versus elapsed time in minutes in the experiment described in Example 1. The horizontal line at 234 $\mu$g/dl represents the capacity by transferrin in plasma to bind soluble iron, and the horizontal line at 125 $\mu$g/dl represents the concentration of iron in the dialysate described in Example 1.

Furthermore, as is demonstrated in Example 1, ferrous gluconate surprisingly transfers into blood from dialysate in an amount substantially higher than that expected based upon the level of transferrin in the blood. Normally, it is expected that blood plasma is able to bind no more iron than that held by transferrin, which is the main iron binding protein in the blood. However, in the experiment set forth in Example 1, a ferrous gluconate concentration (125 $\mu$g/dl) was purposely provided in the dialysate which was less than the transferrin iron binding capacity (234 $\mu$g/dl) in the blood. As is shown in FIG. 1, after only a few minutes of hemodialysis, the transferrin iron level of the blood was reached, and the percent saturation of this iron protein was 100%. Nevertheless, the iron level in the plasma continued to rise over the next half hour or more of dialysis to a level in the plasma which was several times higher than the fully saturated transferrin level, and also much higher than the level of iron in the dialysate (125 $\mu$g/dl).

While it is not intended that the present invention be limited by any mechanism by which it achieves it advantageous result, it appears that ferrous gluconate complexes are bound by another protein in the blood. The mechanism by which this occurs is not known; however, it is evident that the invention enables the delivery of iron complexes from dialysate into blood to much higher levels than previously considered possible. Furthermore, since this iron complex does not become dissolved in blood plasma water, there should be much less threat of toxicity caused by increasing free iron levels in the blood. While this result was achieved by delivering ferrous gluconate to blood from dialysate, it is expected that a wide variety of compositions having similar characteristics to ferrous gluconate would show similar results according to the present invention.

The invention will be further described with reference to the following specific Examples and associated Figures. It will be understood that these Examples are illustrative and not restrictive in nature.

EXAMPLE ONE

Transfer of Ferrous Gluconate into Blood

A two liter volume of bovine blood (hematocrit adjusted from 49 to 40 with saline) which had been stored with heparin anticoagulation for 24 hours was dialyzed using a PAN membrane dialyzer. The volume was maintained at 2 liters throughout the experiment by adding saline. The dialyzer type was FILTRAL 12 and the PAN membranes used had an intrinsic negative charge and, therefore, tended to bind positively charged molecules. The dialysate was created from 20 liters of purified (deionized) water with acetate concentrate (Dial Medical Supply Concentrate Solution for Acetate Dialysate) in a 1:34 dilution with water and 10 mg/L ferrous gluconate (1 mg/dl containing 125 µg/dl iron).

A sample of the blood was taken prior to dialysis of the blood and tested for iron content. The iron content of the pre-dialysis blood was 110 µg/dl and the transferrin iron binding capacity was (234 µg/dl). Dialysis was then started using the following equipment and conditions:

| | |
|---|---|
| Blood Pump: | Minipump Renal Systems at 300 ml/min (setting 323, ¼") |
| Dialysate Pump: | Travenol at 500 ml/min (setting approximately 92) |
| Bath for Dialysate: | 37° C. |

The circuit was primed with dialysate, prepared as described above, pumps were adjusted for proper flow, and then the blood side was drained of dialysate by pulling the Blood In tube out of the dialysis bath and allowing air to fill this side.

Assays were performed to determine plasma iron concentrations at 0, 5, 10, 20 and 30 minutes. A plot of iron concentration in plasma versus elapsed time of this experiment is provided in FIG. 1. Though the iron content of the dialysate was only 125 µg/dl, it was found that a continued transfer of iron into the blood proceeded until the plasma level reached nearly 500 µg/dl after 30 minutes. This transfer indicates an avidity of plasma for the iron complex, even higher than the iron binding capacity of transferrin.

Based upon these results, it is concluded that if the initial rate of iron transfer to the plasma is continued according to this experiment for a period of 180 minutes, approximately 4 mg of iron would be transferred to the plasma. Therefore, to transfer 15 mg of iron to the patient during dialysis, the iron concentration in the dialysate would need to be increased four-fold. As such, increasing the dialysate concentration of ferrous gluconate to 4 mg/dl (with iron concentration of 0.5 µg/dl) will result in transfer of 15 mg of iron per dialysis treatment.

EXAMPLE TWO

Monitoring of Hemolysis in Experimental Dialysis

Figure 2:
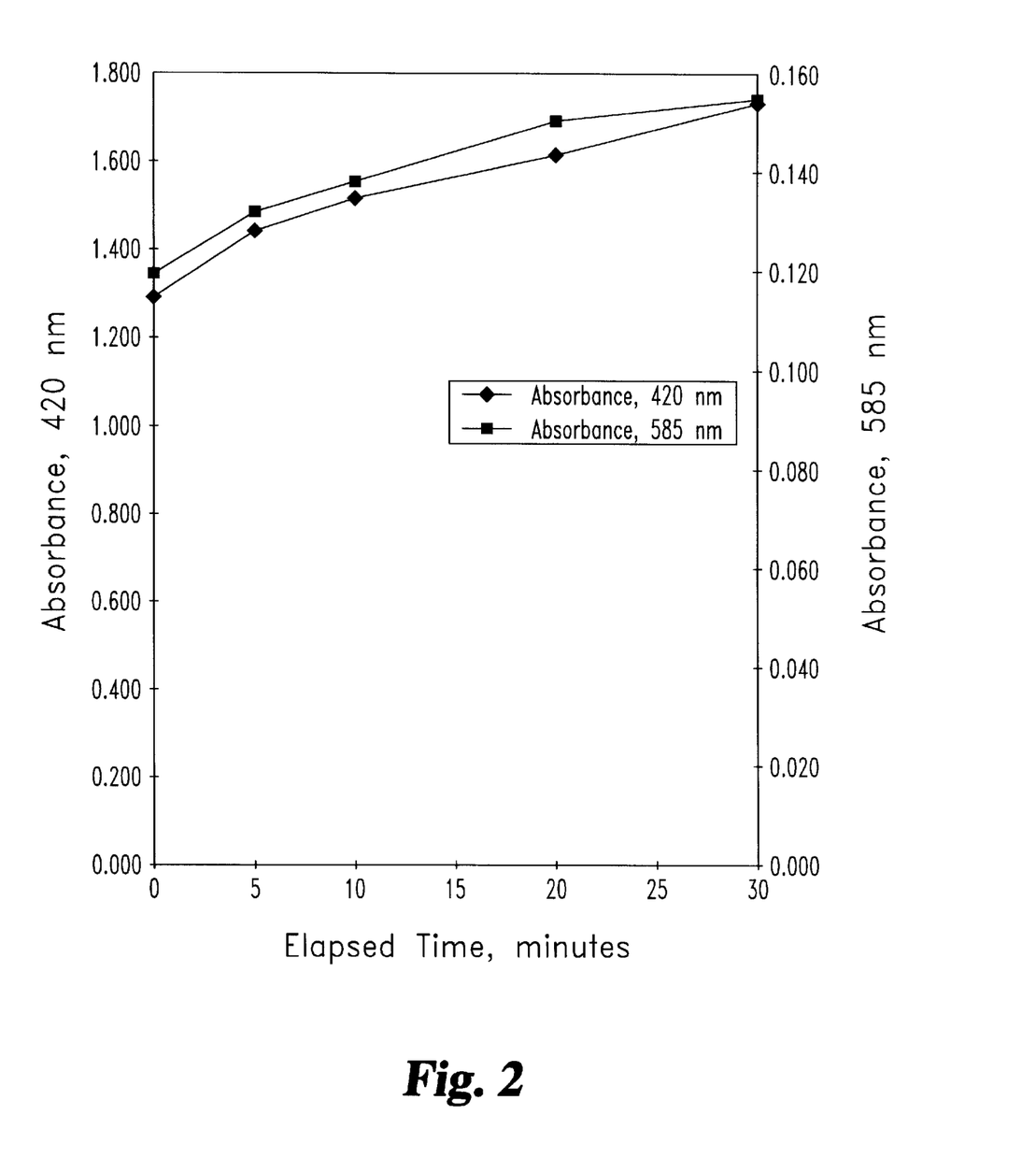
FIG. 2 is a plot of absorbance of plasma at 420 and 585 nm versus elapsed time in minutes, obtained as described in Example 2.

To determine whether the method of Example 1 would cause hemolysis (lysis of red blood cells with the liberation of hemoglobin), absorbance data at 420 and 585 nm was collected for the plasma at various stages of the experiment described in Example 1. These data are provided in FIG. 2. The increase in absorbance indicates that some degree of hemolysis occurred during the experiment; however, this level is not higher than that of similar experiments conducted without iron in the dialysate.

EXAMPLE THREE

Effect on Blood-Leak Detention Systems

Figure 3:
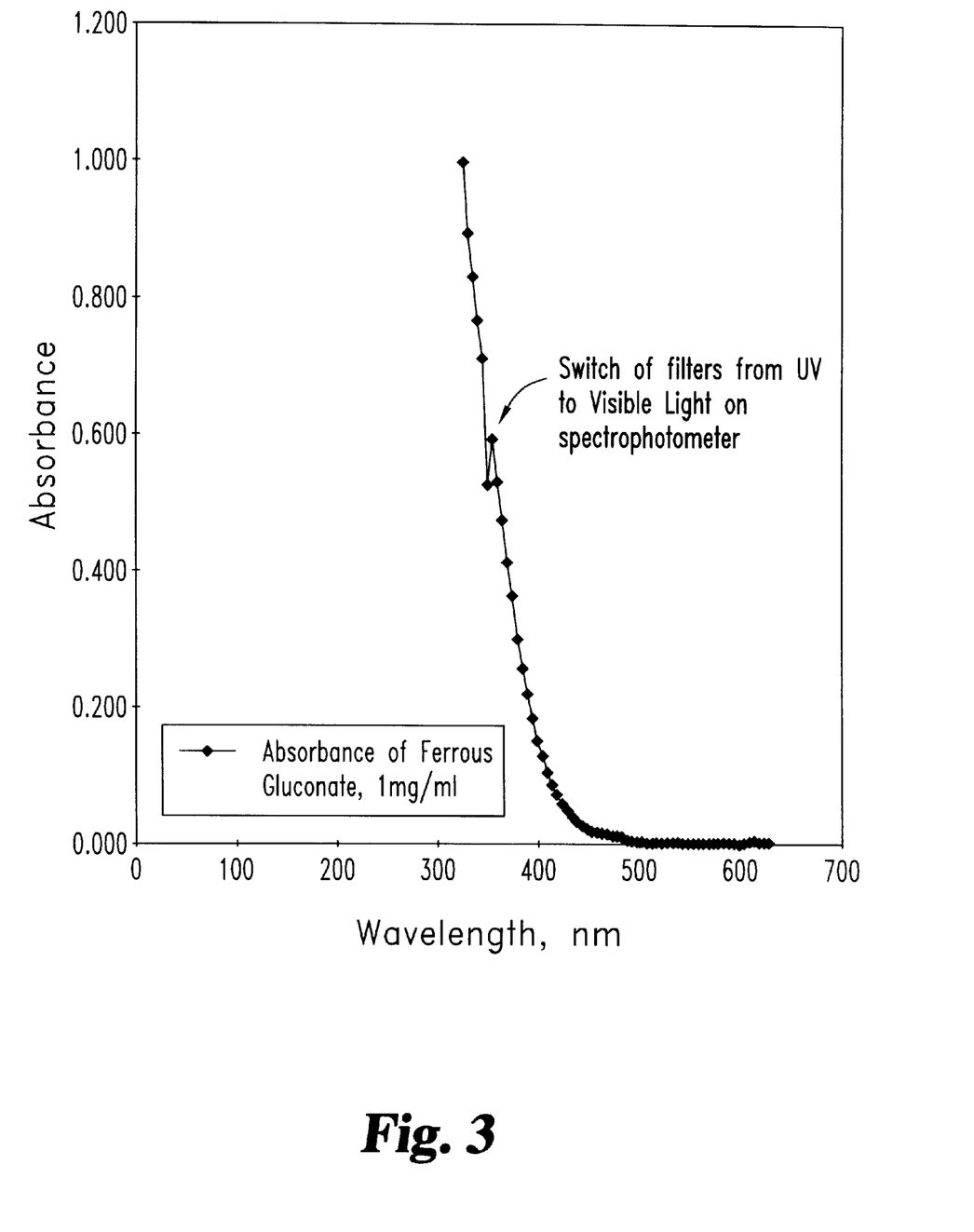
FIG. 3 is a plot of optical absorbance of ferrous gluconate at high concentration (100 mg/dl) versus wavelength (nm), taken for the blood-leak detector experiment described in Example 3.

To determine whether the presence of ferrous gluconate in the dialysate would interfere with blood-leak detection systems used in hemodialysis procedures, optical absorbance data for ferrous gluconate at high concentrations were obtained. These data are provided in FIG. 3. From the plot of FIG. 3, it is apparent that iron can be added to the dialysate without interfering with the detection of hemoglobin in dialysate by blood-leak detectors using optical absorbance at either 420 nm or 585 nm.

While the invention has been described in detail in the foregoing description, the same is to be considered as illustrative and not restrictive in character, it being understood that only the preferred embodiments have been described and that all changes and modifications that come within the spirit of the invention are desired to be protected.

What is claimed is:

1. A method for delivering iron to blood comprising:
   providing a dialysate having dissolved therein a complex of one or more divalent or trivalent iron ions and one or more anions, the complex having a molecular weight of less than about 50,000; and
   dialyzing a patient with the dialysate to increase the level of iron in the patient's blood.

2. The method according to claim 1, wherein the anion is an organic anion.

3. The method according to claim 1, wherein the organic anion has a molecular weight of less than about 12,000.

4. The method according to claim 3, wherein the complex is ferrous gluconate.

5. The method according to claim 1, wherein the molecular weight is less than about 12,000; and wherein said dialyzing comprises dialyzing the blood extracorporeally with the dialysate.

6. The method according to claim 1, wherein said dialyzing comprises introducing the dialysate into the patient's peritoneum.

7. The method according to claim 1, wherein the concentration of divalent or trivalent iron ions in the dialysate is at least about 50 µg/dl and the molecular weight of the complex is less than about 25,000.

8. A method for delivering iron to blood, comprising:
   passing blood against a first side of a membrane; and
   passing against a second side of the membrane an aqueous solution having dissolved therein an iron complex comprising one or more iron ions and one or more anions; the complex having a molecular weight of less than about 12,000;
   wherein the membrane is permeable to the complex; and
   wherein the complex is delivered to the blood.

9. The method according to claim 8, wherein the complex has a molecular weight of less than about 5,000.

10. The method according to claim 8, wherein the complex is ferrous gluconate.

11. A method for delivering iron to a patient, comprising:
    introducing a dialysate into a patient's peritoneal cavity, the dialysate having dissolved therein a complex of one or more divalent or trivalent iron ions and one or more anions;

wherein the complex has a molecular weight of less than about 50,000.

12. The method according to claim 11, wherein the complex has a molecular weight of less than about 25,000.

13. The method according to claim 11, wherein the anion is an organic anion.

14. A method for the treatment of a patient to increase the level of iron in the patient's bloodstream, which comprises performing dialysis on the patient with a dialysate which comprises a soluble, low molecular weight iron complex; sodium; magnesium; calcium; potassium; chloride; acetate and bicarbonate.

15. A method for delivering iron to blood comprising:
    providing a dialysate having dissolved therein from about 0.008 to about 2 mg/dl ferrous gluconate; and
    dialyzing a patient with the dialysate to increase the level of iron in the patient's blood.

16. The method according to claim 15, wherein the dialysate further comprises from about 130 to about 150 mEq/L sodium, from about 0.4 to about 1.5 mEq/L magnesium, from about 2 to about 4 mEq/L calcium, from about 1 to about 3 mEq/L potassium, from about 90 to about 120 mEq/L chloride, from about 3 to about 5 mEq/L acetate and from about 30 to about 40 mEq/L bicarbonate.

17. A composition comprising an aqueous medium having dissolved therein sodium, magnesium, calcium, potassium, chloride, acetate, bicarbonate and an iron complex having a molecular weight of less than about 50,000.

18. The composition according to claim 17, further comprising a member selected from the group consisting of dextrose, a sorbent and a surfactant.

19. The composition according to claim 17, comprising from about 130 to about 150 mEq/L sodium, from about 0.4 to about 1.5 mEq/L magnesium, from about 2 to about 4 mEq/L calcium, from about 1 to about 3 mEq/L potassium, from about 90 to about 120 mEq/L chloride, from about 3 to about 5 mEq/L acetate, from about 30 to about 40 mEq/L bicarbonate and from about 1 to about 250 $\mu$g/dl iron as an iron complex having a molecular weight of less than about 50,000.

20. The composition according to claim 17, comprising from about 3900 to about 6000 mEq/L sodium, from about 12 to about 60 mEg/L magnesium, from about 60 to about 160 mEq/L calcium, from about 30 to about 120 mEq/L potassium, from about 2700 to about 4800 mEq/L chloride, from about 90 to about 200 mEq/L acetate, from about 900 to about 1600 mEq/L bicarbonate and from about 0.03 to about 10 mg/dl iron as an iron complex having a molecular weight of less than about 50,000.

* * * * *

(12) EX PARTE REEXAMINATION CERTIFICATE (7376th)
United States Patent
Ash (10) Number: US 5,906,978 C1
(45) Certificate Issued: Feb. 23, 2010

(54) METHOD FOR IRON DELIVERY TO A PATIENT BY TRANSFER FROM DIALYSATE

(75) Inventor: Stephen R. Ash, Lafayette, IN (US)

(73) Assignee: Hemocleanse, Inc., Lafayette, IN (US)

Reexamination Request:
No. 90/009,165, May 30, 2008

Reexamination Certificate for:
Patent No.: 5,906,978
Issued: May 25, 1999
Appl. No.: 08/869,331
Filed: Jun. 5, 1997

Related U.S. Application Data

(60) Provisional application No. 60/023,926, filed on Aug. 14, 1996.

(51) Int. Cl.
*A61K 33/26* (2006.01)
*A61M 1/16* (2006.01)

(52) U.S. Cl. .......................... 514/23; 424/648; 514/502; 514/814

(58) Field of Classification Search ........................ None
See application file for complete search history.

(56) References Cited

U.S. PATENT DOCUMENTS 4,202,760 A 5/1980 Storey et al.
6,689,275 B1 2/2004 Gupta

*Primary Examiner*—Evelyn Huang (57) ABSTRACT

The invention relates to methods and compositions for delivering iron to an iron-deficient patient, more particularly, to methods whereby an iron complex comprising divalent or trivalent ionic iron complexed with one or more low molecular weight anions is administered to a patient by transfer from dialysate. A complex selected according to the invention is non-polymeric; soluble in an aqueous medium; chemically stable, thereby preventing the dissociation of iron ions from the anions under conditions according to the invention; and can be well absorbed into blood and the living body. Also provided are dialysate compositions including therein an iron complex selected according to the invention, and dialysate concentrates which may be diluted to yield an inventive dialysate composition.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1, 3, 5–9, 11, 12, 14 and 17–20 are cancelled.
Claims 2, 4, 10, 13 and 15–16 were not reexamined.

\* \* \* \* \*